United States Patent
Goorevich et al.

(10) Patent No.: US 10,091,591 B2
(45) Date of Patent: Oct. 2, 2018

(54) ELECTRO-ACOUSTIC ADAPTION IN A HEARING PROSTHESIS

(71) Applicant: Cochlear Limited, Macquarie University, NSW (AU)

(72) Inventors: Michael Goorevich, Naremburn (AU); Zachary Mark Smith, Greenwood Village, CO (US)

(73) Assignee: Cochlear Limited, Macquarie University, NSW (AU)

( * ) Notice: Subject to any disclaimer, the term of this patent is extended or adjusted under 35 U.S.C. 154(b) by 114 days.

(21) Appl. No.: 15/176,538

(22) Filed: Jun. 8, 2016

(65) Prior Publication Data
US 2017/0359661 A1 Dec. 14, 2017

(51) Int. Cl.
*H04R 25/00* (2006.01)
*A61N 1/36* (2006.01)
*G10L 25/78* (2013.01)

(52) U.S. Cl.
CPC ....... *H04R 25/505* (2013.01); *A61N 1/36032* (2013.01); *G10L 25/78* (2013.01); *H04R 25/356* (2013.01); *H04R 25/606* (2013.01); *H04R 25/70* (2013.01)

(58) Field of Classification Search
CPC .... A61B 5/04; A61B 5/12; A61N 1/05; A61N 1/36; H04R 26/00; H04R 25/70
USPC .......................................... 607/3, 55, 56, 57
See application file for complete search history.

(56) References Cited

U.S. PATENT DOCUMENTS

| | | |
|---|---|---|
| 2005/0129262 A1 | 6/2005 | Dillon et al. |
| 2011/0004273 A1 | 1/2011 | Van den Heuvel et al. |
| 2011/0280427 A1 | 11/2011 | Buyens |
| 2012/0290045 A1* | 11/2012 | Nicolai ................. H04R 25/70 607/57 |
| 2013/0006328 A1 | 1/2013 | Bouchataoui et al. |
| 2015/0016614 A1 | 1/2015 | Buyens |
| 2015/0271612 A1* | 9/2015 | Menzl .................... H04R 25/70 607/3 |

FOREIGN PATENT DOCUMENTS

KR    10-1499089 B1    12/2014

OTHER PUBLICATIONS

International Search Report and Written Opinion in corresponding International Application No. PCT/IB2017/0532497 dated Sep. 22, 2017, 11 pages.

* cited by examiner

*Primary Examiner* — Brian Ensey
(74) *Attorney, Agent, or Firm* — Edell, Shapiro & Finnan, LLC (57) ABSTRACT

Presented herein are techniques for dynamically setting, in real-time, a ratio of acoustical stimulation signals to electrical stimulation signals delivered by a hearing prosthesis. The ratio of the acoustical stimulation signals to the electrical stimulation signals is set based on one or more characteristics or attributes of the input sound signals that are received and processed by the hearing prosthesis in order to generate the acoustical and electrical stimulation signals.

26 Claims, 6 Drawing Sheets

ELECTRO-ACOUSTIC ADAPTION IN A HEARING PROSTHESIS

BACKGROUND

Field of the Invention

The present invention relates generally to hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: determining one or more attributes of sound signals received at a hearing prosthesis worn by a recipient; generating, based on the received sound signals, acoustical stimulation signals and electrical stimulation signals; and setting a ratio of the acoustical stimulation signals to the electrical stimulation signals based on the one or more attributes of the sound signals.

In another aspect, a hearing prosthesis is provided. The hearing prosthesis comprises: one or more sound input elements configured to receive sound signals; an electric sound processing path configured to convert at least a first portion of the sound signals into one or more output signals for use in delivering electrical stimulation to a recipient; an acoustic sound processing path configured to convert at least a second portion of the sound signals into one or more output signals for use in delivering acoustical stimulation to the recipient; and an electro-acoustic adaption module configured to alter a relative perceptual loudness of at least one of the electrical stimulation and the acoustic stimulation based on one or more attributes of the sound signals.

In another aspect, a hearing prosthesis is provided. The hearing prosthesis comprises: one or more sound input elements configured to receive sound signals; and one or more processors configured to generate output signals representative of acoustical stimulation signals and electrical stimulation signals for delivery to a recipient of the hearing prosthesis, wherein at least one of a relative level and a relative loudness of the acoustical stimulation signals to the electrical stimulation signals is set based on one or more characteristics of the sound signals.

BRIEF DESCRIPTION OF THE DRAWINGS

Embodiments of the present invention are described herein in conjunction with the accompanying drawings, in which.

DETAILED DESCRIPTION

Auditory/hearing prosthesis recipients suffer from different types of hearing loss (e.g., conductive and/or sensorineural) and/or different degrees/severity of hearing loss. However, it is now common for many hearing prosthesis recipients to retain some residual natural hearing ability (residual hearing) after receiving the hearing prosthesis. For example, progressive improvements in the design of intra-cochlear electrode arrays (stimulating assemblies), surgical implantation techniques, tooling, etc. have enabled atraumatic surgeries which preserve at least some of the recipient's fine inner ear structures (e.g., cochlea hair cells) and the natural cochlea function, particularly in the higher frequency regions of the cochlea.

Due, at least in part, to the ability to preserve residual hearing, the number of recipients who are candidates for different types of implantable hearing prostheses, particularly electro-acoustic hearing prostheses, has continued to expand. Electro-acoustic hearing prostheses are medical devices that deliver both acoustical stimulation (i.e., acoustical stimulation signals) and electrical stimulation (i.e., electrical stimulation signals), possibly simultaneously, to the same ear of a recipient. Typically, due to the limits of residual hearing in the implanted ear, the acoustical stimulation is used to present sound signal components corresponding to the lower frequencies of input sound signals (as determined from the residual hearing capabilities of the implanted ear), while the electrical stimulation is used to present sound signal components corresponding to the higher frequencies. The tonotopic region of the cochlea where the sound or stimulation output transitions from the acoustical stimulation to the electric stimulation is called the cross-over frequency region.

Recipients of electro-acoustic hearing prostheses typically benefit from having the acoustical stimulation in addition to the electrical stimulation, as the acoustical stimulation adds a more "natural" sound to their hearing perception over the electrical stimulation signals only in that ear. The addition of the acoustical stimulation can, in some cases, also provide improved pitch and music perception and/or appreciation, as the acoustic signals may contain a more salient lower frequency (e.g., fundamental pitch, F0) representation than is possible with electrical stimulation. Other benefits of electro-acoustic hearing prosthesis may include, for example, improved sound localization, binaural release from unmasking, the ability to distinguish acoustic signals in a noisy environment, etc.

In an electro-acoustic hearing prosthesis, the acoustical stimulation signals and the electrical stimulation signals are each generated and delivered to a recipient at a predetermined/preset level (e.g., amplitude) and/or a predetermined/preset estimated perceptual loudness (loudness). The relative level and/or relative loudness of the acoustical stimulation signals to the electrical stimulation signals (and vice versa) are collectively and generally referred to herein as the "ratio" of the acoustical stimulation signals to the electric stimulation signals. Presented herein are techniques to automatically set one or more of the relative level or relative loudness of the acoustical stimulation signals to the electrical stimulation signals (i.e., dynamically set the ratio of the acoustical and electrical stimulation signals). As described further below, the relative level or relative loudness of the acoustical stimulation signals to the electrical stimulation signals is set, in real-time, based on one or more characteristics or attributes of the sound signals that are received and processed by the electro-acoustic hearing prosthesis to generate the acoustical and electrical stimulation signals.

For ease of illustration, embodiments are primarily described herein with reference to one specific type of hearing prosthesis, namely an electro-acoustic hearing prosthesis comprising a cochlear implant portion and a hearing aid portion. However, it is to be appreciated that the techniques presented herein may be used with other types of hearing prostheses, such as bi-modal hearing prostheses, electro-acoustic hearing prosthesis comprising other types of output devices (e.g., auditory brainstem stimulators, direct acoustic stimulators, bone conduction devices, etc.).

Figure 1A:
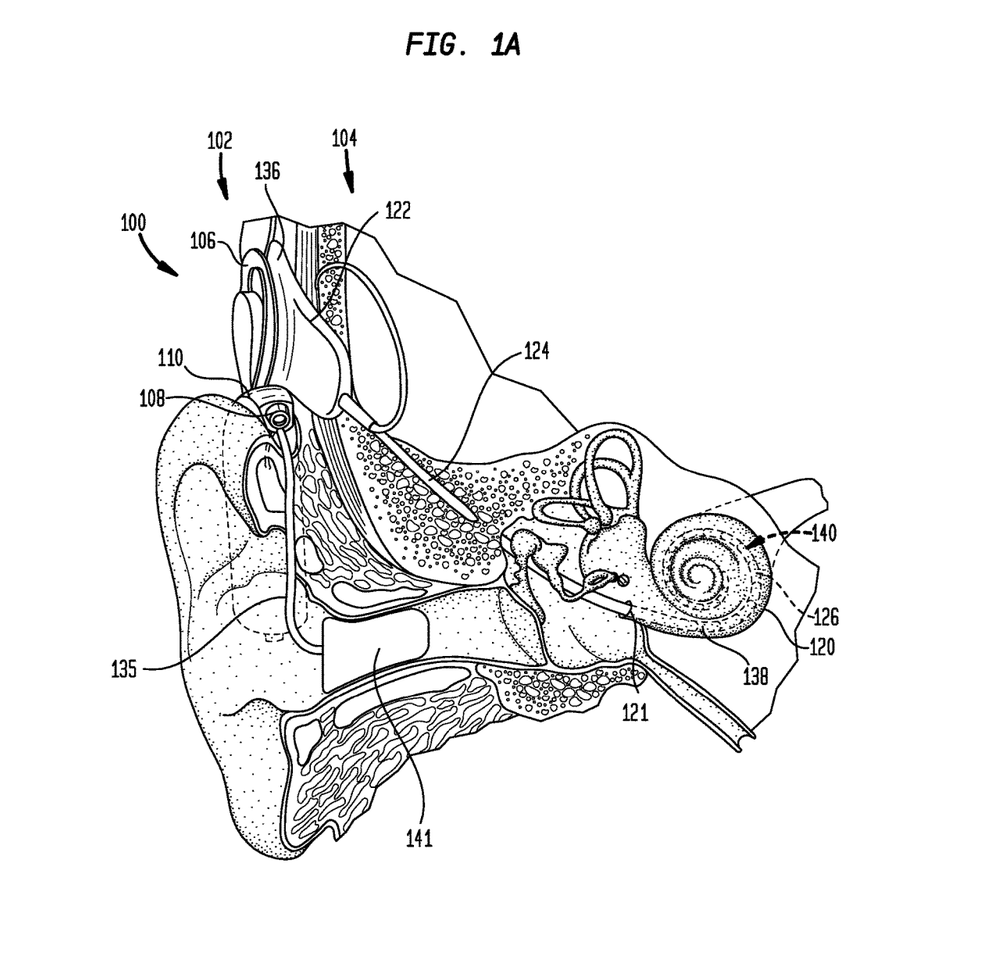
FIG. 1A is a schematic diagram illustrating an electro-acoustic hearing prosthesis in accordance with embodiments presented herein.
Figure 1B:
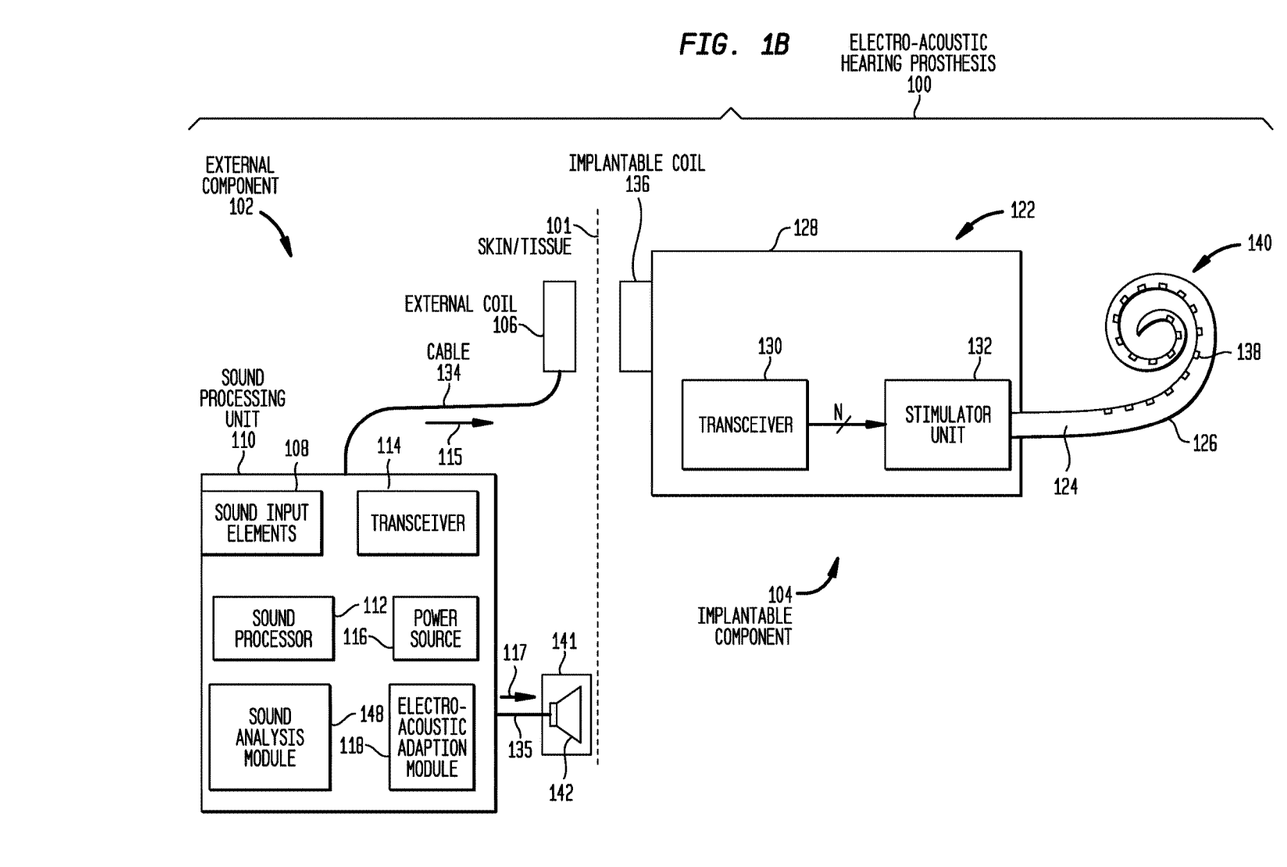
FIG. 1B is a block diagram of the electro-acoustic hearing prosthesis of FIG. 1A.

FIG. 1A is schematic diagram of an exemplary electro-acoustic hearing prosthesis 100 configured to implement embodiments of the present invention, while FIG. 1B is a block diagram of the electro-acoustic hearing prosthesis. The electro-acoustic hearing prosthesis 100 includes an external component 102 and an internal/implantable component 104.

The external component 102 is directly or indirectly attached to the body of the recipient and comprises a sound processing unit 110, an external coil 106, and, generally, a magnet (not shown in FIG. 1A) fixed relative to the external coil 106. The external coil 106 is connected to the sound processing unit 110 via a cable 134. The sound processing unit 110 comprises one or more sound input elements 108 (e.g., microphones, audio input ports, cable ports, telecoils, a wireless transceiver, etc., a sound processor 112, an external transceiver unit (transceiver) 114, a power source 116, an electro-acoustic adaption module 118, and a sound analysis module 148. The sound processing unit 110 may be, for example, a behind-the-ear (BTE) sound processing unit, a body-worn sound processing unit, a button sound processing unit, etc.

Connected to the sound processing unit 110 is a hearing aid component 141 that is connected to the sound processing unit 110 via a cable 135. The hearing aid component 141 includes a receiver 142 (FIG. 1B) that may be, for example, positioned in or near the recipient's outer ear. The receiver 142 is an acoustic transducer that is configured to deliver acoustic signals (acoustical stimulation signals) to the recipient via the recipient's ear canal and middle ear.

FIGS. 1A and 1B illustrate the use of a receiver 142 to deliver acoustic stimulation to the recipient. However, it is to be appreciated that other types of devices may be used in other embodiments to deliver the acoustic stimulation. For example, other embodiments may include an external or implanted vibrator that is configured to deliver acoustic stimulation to the recipient.

As shown in FIG. 1B, the implantable component 104 comprises an implant body (main module) 122, a lead region 124, and an elongate intra-cochlear stimulating assembly 126. The implant body 122 generally comprises a hermetically-sealed housing 128 in which an internal transceiver unit (transceiver) 130 and a stimulator unit 132 are disposed. The implant body 122 also includes an internal/implantable coil 136 that is generally external to the housing 128, but which is connected to the transceiver 130 via a hermetic feedthrough (not shown in FIG. 1B). Implantable coil 136 is typically a wire antenna coil comprised of multiple turns of electrically insulated single-strand or multi-strand platinum or gold wire. The electrical insulation of implantable coil 136 is provided by a flexible molding (e.g., silicone molding), which is not shown in FIG. 1B. Generally, a magnet is fixed relative to the implantable coil 136.

Elongate stimulating assembly 126 is configured to be at least partially implanted in the recipient's cochlea 120 (FIG. 1B) and includes a plurality of longitudinally spaced intra-cochlear electrical stimulating contacts (electrodes) 138 that collectively form a contact array 140 for delivery of electrical stimulation (current) to the recipient's cochlea. In certain arrangements, the contact array 140 may include other types of stimulating contacts, such as optical stimulating contacts, in addition to the electrodes 138.

Stimulating assembly 126 extends through an opening 121 in the cochlea (e.g., cochleostomy, the round window, etc.) and has a proximal end connected to stimulator unit 132 via lead region 124 and a hermetic feedthrough (not shown in FIG. 1B). Lead region 124 includes a plurality of conductors (wires) that electrically couple the electrodes 138 to the stimulator unit 132.

Returning to external component 102, the sound input element(s) 108 are configured to detect/receive input sound signals and to generate electrical output signals therefrom. The sound processor 112 is configured execute sound processing and coding to convert the output signals received from the sound input elements into coded data signals that represent acoustical and/or electrical stimulation for delivery to the recipient. That is, as noted, the electro-acoustic hearing prosthesis 100 operates to evoke perception by the recipient of sound signals received by the sound input elements 108 through the delivery of one or both of electrical stimulation signals and acoustical stimulation signals to the recipient. As such, depending on a variety of factors, the sound processor 112 is configured to convert the output signals received from the sound input elements into a first set of output signals representative of electrical stimulation and/or into a second set of output signals representative of acoustical stimulation. The output signals representative of electrical stimulation are represented in FIG. 1B by arrow 115, while the output signals representative of acoustical stimulation are represented in FIG. 1B by arrow 117.

The output signals 115 are provided to the transceiver 114. The transceiver 114 is configured to use the output signals 115 to transcutaneously transfer coded signals to the implantable component 104 via external coil 106. More specifically, the magnets fixed relative to the external coil 106 and the implantable coil 136 facilitate the operational alignment of the external coil 106 with the implantable coil 136. This operational alignment of the coils enables the external coil 106 to transmit the coded data signals, as well as power signals received from power source 116, to the implantable coil 136. In certain examples, external coil 106 transmits the signals to implantable coil 136 via a radio frequency (RF) link. However, various other types of energy transfer, such as infrared (IR), electromagnetic, capacitive and inductive transfer, may be used to transfer the power and/or data from an external component to an electro-acoustic hearing prosthesis and, as such, FIG. 1B illustrates only one example arrangement.

In general, the coded data and power signals are received at the transceiver 130 and provided to the stimulator unit 132. The stimulator unit 132 is configured to utilize the coded data signals to generate electrical stimulation signals (e.g., current signals) for delivery to the recipient's cochlea via one or more stimulating contacts 138. In this way, electro-acoustic hearing prosthesis 100 electrically stimulates the recipient's auditory nerve cells, bypassing absent or defective hair cells that normally transduce acoustic vibrations into neural activity, in a manner that causes the recipient to perceive one or more components of the received sound signals.

As noted above, it is common for hearing prosthesis recipients to retain at least part of this normal hearing functionality (i.e., retain at least some residual hearing). Therefore, the cochlea of a hearing prosthesis recipient can be acoustically stimulated upon delivery of a sound signal to the recipient's outer ear. In the example of FIGS. 1A and 1B, the receiver 142 is used to aid the recipient's residual hearing. More specifically, the output signals 117 (i.e., the signals representative of acoustical stimulation) are provided to the receiver 142. The receiver 142 is configured to utilize the output signals 117 to generate the acoustical stimulation signals that are provided to the recipient. In other words, the receiver 142 is used to enhance, and/or amplify a sound signal which is delivered to the cochlea via the middle ear bones and oval window, thereby creating waves of fluid motion of the perilymph within the cochlea.

In conventional electro-acoustic hearing prostheses, the acoustical stimulation signals and the electrical stimulation signals are each generated and delivered to a recipient with a predetermined level and/or loudness. In accordance with embodiments of the present invention, the electro-acoustic hearing prosthesis 100 of FIGS. 1A and 1B includes an electro-acoustic adaption module 118 that is configured to dynamically set a ratio of the acoustical stimulation signals to the electrical stimulation signals based on one or more attributes of the input sound signals (i.e., the sounds received by the sound inputs 108 and used to generate the acoustical and electrical stimulation signals). Stated differently, the electro-acoustic adaption module 118 is configured to automatically adjust, in real-time, one or more operations that control the level (e.g., amplitude) of the acoustical stimulation signals and/or the electrical stimulation signals, or automatically adjust, in real-time, one or more processing operations that control the perceptual loudness of the acoustical stimulation signals and/or the electrical stimulation signals. As a result, the electro-acoustic adaption module 118 is referred to herein as being configured to adjust or adapt the relative level and/or relative loudness of the acoustical stimulation signals to the electrical stimulation signals. The one or more attributes of the sound signals that are the basis for setting the ratio of the acoustical stimulation signals to the electrical stimulation signal are determined by the sound analysis module 148. Further details of the sound analysis module 148 and the electro-acoustic adaption module 118 are provided below.

FIGS. 1A and 1B illustrate an arrangement in which the cochlear implant 100 includes an external component 102. However, it is to be appreciated that embodiments of the present invention may be implemented in cochlear implants having alternative arrangements.

Figure 2:
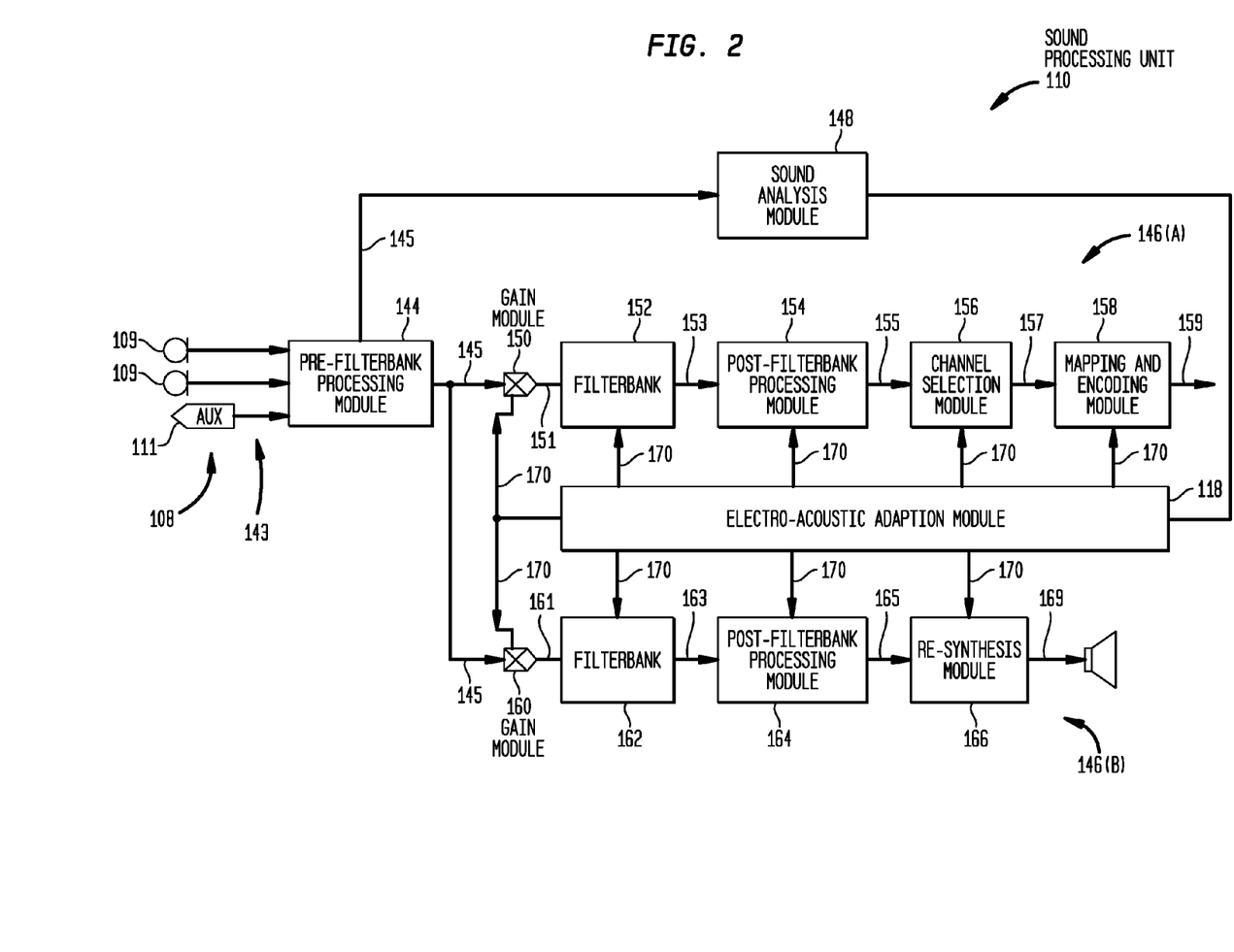
FIG. 2 is a diagram illustrating a sound processing unit that in accordance with embodiments presented herein.

FIG. 2 is a schematic diagram illustrating an example arrangement for the sound processing unit 110 in accordance with embodiments presented herein. For ease of illustration, only elements of the sound processing unit 110 related to the electro-acoustic adaption techniques presented herein, namely the sound input elements 108, the sound processor 112, the electro-acoustic adaption module 118, and the sound analysis module 148 are shown in FIG. 2.

As noted, the electro-acoustic hearing prosthesis 100 comprises one or more sound input elements 108. In this example, the sound input elements 108 comprise two microphones 109 and at least one auxiliary input 111 (e.g., an audio input port, a cable port, a telecoil, a wireless transceiver, etc.). If not already in an electrical form, sound input elements 108 convert received sound signals into electrical signals 143, referred to herein as electrical output signals, that represent the received sound signals. As shown in FIG. 2, the electrical output signals 143 are provided to a pre-filterbank processing module 144.

The pre-filterbank processing module 144 is configured to, as needed, combine the electrical output signals 143 received from the sound input elements 108 and prepare those signals for subsequent processing. The pre-filterbank processing module 144 then generates a pre-filtered output signal 145 that, as described further below, is the basis of further processing operations. The pre-filtered output signal 145 represents the collective sound signals received at the sound input elements 108 at a given point in time.

As noted, the electro-acoustic hearing prosthesis 100 is configured to deliver both acoustical stimulation (i.e., acoustical stimulation signals) and electrical stimulation (i.e., electrical stimulation signals) to a recipient. Acoustical stimulation combined with electrical stimulation is sometimes referred to herein as electro-acoustic stimulation. As such, the sound processor 112 is generally configured to execute sound processing and coding to convert the pre-filtered output signal 145 into output signals that represent acoustical or electrical stimulation for delivery to the recipient. This is shown in FIG. 2 where the sound processor 112 includes two parallel sound processing paths 146(A) and 146(B). The first sound processing path 146(A) is an electric sound processing path, sometimes referred to herein as a cochlear implant sound processing path, that is configured to generate, from at least a first portion/segment of the pre-filtered output signal 145, output signals for use in electrically stimulating the recipient. The second sound processing path 146(B) is an acoustic sound processing path, sometimes referred to herein as a hearing aid sound processing path, that is configured to generate, from at least a second portion of the pre-filtered output signal 145, output signals for use in acoustically stimulating the recipient.

The sound processing path 146(A) (i.e., electric sound processing path) comprises a gain module 150, a filterbank 152, a post-filterbank processing module 154, a channel selection module 156, and a channel mapping module 158. The sound processing path 146(B) (i.e., acoustic sound processing path) comprises a gain module 160, a filterbank 162, a post-filterbank processing module 164, and a re-synthesis module 168.

Referring first to the sound processing path 146(A), the pre-filtered output signal 145 generated by the pre-filterbank processing module 144 is provided to the gain module 150 that applies a gain adjustment (e.g., a broad-band gain adjustment) thereto. The gain module 150 provides a gain-adjusted signal 151 to the filterbank 152.

The filterbank 152 uses the gain-adjusted signal 151 to generate a suitable set of bandwidth limited channels, or frequency bins, that each includes a spectral component of the received sound signals that are to be utilized for subsequent sound processing in path 146(A). That is, the filterbank 152 is a plurality of band-pass filters that separates the gain-adjusted signal 151 into multiple components, each one carrying a single frequency sub-band of the original signal (i.e., frequency components of the received sounds signal as included in pre-filtered output signal 145 and gain-adjusted signal 151).

The channels created by the filterbank 152 are sometimes referred to herein as sound processing channels, and the sound signal components within each of the sound processing channels are sometimes referred to herein as band-pass filtered signals or channelized signals. As described further below, the band-pass filtered or channelized signals created by the filterbank 152 may be adjusted/modified as they pass through the electric sound processing path 146(A). As such, the band-pass filtered or channelized signals are referred to differently at different stages of the electric sound processing path 146(A). However, it will be appreciated that reference herein to a band-pass filtered signal or a channelized signal may refer to the spectral component of the received sound signals at any point within the electric sound processing path 146(A) (e.g., pre-processed, processed, selected, etc.).

At the output of the filterbank 152, the channelized signals are initially referred to herein as pre-processed signals 153. The number 'm' of channels and pre-processed signals 153 generated by the filterbank 152 may depend on a number of different factors including, but not limited to, implant design, number of active electrodes, coding strategy, and/or recipient preference(s). In certain arrangements, twenty-two (22) channelized signals are created and the electric sound processing path 146(A) is said to include 22 channels.

The pre-processed signals 153 are provided to the post-filterbank processing module 154. The post-filterbank processing module 156 is configured to perform a number of sound processing operations on the pre-processed signals 154. These sound processing operations include, for example, channelized gain adjustments for hearing loss compensation (e.g., gain adjustments to one or more discrete frequency ranges of the sound signals), noise reduction operations, speech enhancement operations, etc., in one or more of the channels. After performing the sound processing operations, the post-filterbank processing module 154 outputs a plurality of processed channelized signals 155.

As noted, in the specific arrangement of FIG. 2, the electric sound processing path 146(A) includes a channel selection module 156. The channel selection module 156 is configured to perform a channel selection process to select, according to one or more selection rules, which of the 'm' channels should be use in hearing compensation. The signals selected at channel selection module 156 are represented in FIG. 2 by arrow 157 and are referred to herein as selected channelized signals or, more simply, selected signals.

In the embodiment of FIG. 2, the channel selection module 156 selects a subset 'n' of the 'm' processed channelized signals 155 for use in generation of electrical stimulation for delivery to a recipient (i.e., the sound processing channels are reduced from 'm' channels to 'n' channels). In one specific example, the 'n' largest amplitude channels (maxima) from the 'm' available combined channel signals/masker signals is made, with 'm' and 'n' being programmable during initial fitting, and/or operation of the prosthesis. It is to be appreciated that different channel selection methods could be used, and are not limited to maxima selection.

It is also to be appreciated that, in certain embodiments, the channel selection module 156 may be omitted. For example, certain arrangements may use a continuous interleaved sampling (CIS), CIS-based, or other non-channel selection sound coding strategy.

The electric sound processing path 146(A) also comprises the channel mapping module 158. The channel mapping module 158 is configured to map the amplitudes of the selected signals 157 (or the processed channelized signals 155 in embodiments that do not include channel selection) into a set of output signals (e.g., stimulation commands) that represent the attributes of the electrical stimulation signals that are to be delivered to the recipient so as to evoke perception of at least a portion of the received sound signals. This channel mapping may include, for example, threshold and comfort level mapping, dynamic range adjustments (e.g., compression), volume adjustments, etc., and may encompass sequential and/or simultaneous stimulation paradigms.

In the embodiment of FIG. 2, the set of stimulation commands that represent the electrical stimulation signals are encoded for transcutaneous transmission (e.g., via an RF link) to an implantable component 104 (FIGS. 1A and 1B). This encoding is performed, in the specific example of FIG. 2, at channel mapping module 158. As such, channel mapping module 158 is sometimes referred to herein as a channel mapping and encoding module and operates as an output block configured to convert the plurality of channelized signals into a plurality of output signals 159.

Referring next to acoustic sound processing path 146(B), the pre-filtered output signal 145 generated by the pre-filterbank processing module 144 is also provided to the gain module 160 that applies a gain adjustment (e.g., a broad-band gain adjustment) thereto. The gain module 160 provides a gain-adjusted signal 161 to the filterbank 162. Similar to the filterbank 152, the filterbank 162 uses the gain-adjusted signal 161 to generate a suitable set of bandwidth limited (channelized) signals, sometimes referred to herein as a band-pass filtered signals, which represent the spectral components of the received sounds signal that are to be utilized for subsequent hearing aid sound processing. That is, the filterbank 162 is a plurality of band-pass filters that separates the pre-filtered output signal 145 into multiple components, each one carrying a frequency sub-band of the original signal. The channelized signals are referred to herein as being separated into, or forming, different sound processing channels. The number 'y' of channels and channelized signals generated by the filterbank 162 may depend on a number of different factors including, but not limited to, processing strategy, gain models, residual hearing (or loss), recipient preference(s), etc. In certain examples, the channels generated by the filterbank 162 are substantially similar to the channels created by the filterbank 152, while in other examples the number of channels, frequency range of the channels, etc. created by the filterbank 162 are different from the channels created by the filterbank 152.

At the output of the filterbank 162, the channelized signals are referred to as pre-processed signals 163. The pre-processed signals 163 are provided to the post-filterbank processing module 164. The post-filterbank processing module 164 is configured to perform a number of sound processing operations on the pre-processed signals 163. These sound processing operations include, for example gain adjustments for hearing loss compensation, noise reduction operations, speech enhancement operations, etc., in one or more of the channels. After performing the sound processing operations, the post-filterbank processing module 164 outputs a plurality of processed channelized signals 165.

As noted, the acoustic sound processing path 146(B) terminates at the re-synthesis module 166. The re-synthesis module 166 generates, from the processed channelized signals 165, one or more output signals 169. The output signals 169 are used to drive an electroacoustic transducer, such as the receiver 142, so that the transducer generates an acoustic signal for delivery to the recipient. In other words, the acoustic sound processing path 146(B) generates one or more output signals 169 in the form of electroacoustic transducer drive signals. Although not shown in FIG. 2, one or more operations may be performed after the re-synthesis operations of re-synthesis module 166 and before the signal is sent to the receiver 142. For example, a limiter or compressor, a maximum power output (MPO) stage, etc. could be added between the re-synthesis module 166 and the receiver 142.

As noted, the acoustical stimulation signals and the electrical stimulation signals generated by an electro-acoustic hearing prosthesis each have a selected level and/or a selected loudness. Also as noted above, the electro-acoustic adaption module 118 is configured to automatically set one or more of the relative level or relative loudness of the acoustical stimulation signals to the electrical stimulation signals (i.e., set the ratio of the acoustical and electrical stimulation signals) based on one or more sound signal attributes determined by the sound analysis module 148.

More specifically, the input sound signals received by the sound input elements are provided to the sound analysis module 148. For example, as shown in the embodiment of FIG. 2, the pre-filterbank processing module 144 is configured to provide the pre-filtered output signal 145 to the sound analysis module 148. Although FIG. 2 illustrates that the sound analysis module 148 receives the sound signals as part of the pre-filtered output signal 145, in other embodiments the sound analysis module 148 may receive the sound signals directly from the sound input elements (i.e., the sound analysis module 148 may receive the electrical output signals 143).

The sound analysis module 148 is configured to evaluate/analyze the received sound signals to determine one or more characteristics/attributes of the sound signals. For example, the sound analysis module 148 may be configured to determine an input level of the sound signals. Alternatively, the sound analysis module 148 may be configured to perform voice activity detection (VAD), also known as speech activity detection or speech detection, to detect the presence (or absence) of human speech in the sound signals. In further embodiments, the sound analysis module 148 is configured to perform environmental classification operations. That is, the sound analysis module 148 is configured to use the sound signals to "classify" the ambient sound environment and/or the sound signals into one or more sound categories (e.g., determine the input signal type). In other words, the sound analysis module 148 may be configured to determine the "type" of the received sound signals. The categories may include, but are not limited to, "Speech," "Noise," "Speech+Noise," or "Music."

The sound analysis module 148 is configured to provide the electro-acoustic adaption module 118 with information relating to the sound signal attributes determined from the received sound signals. The electro-acoustic adaption module 118 is configured to use the sound signal attributes to dynamically set, in real-time, the ratio (e.g., relative level and/or loudness) of the acoustical stimulation signals to the electrical stimulation signals (and vice versa) that are generated from, and are representative of, the received sound signals.

More specifically, as noted above, the output signals 159 generated by the electric sound processing path 146(A) are useable to generate electrical stimulation signals for delivery to the recipient. Similarly, the output signals 169 generated by the acoustic sound processing path 146(B) are useable to generate acoustical stimulation signals for delivery to the recipient. As such, the electro-acoustic adaption module 118 dynamically sets (i.e., adjusts) the ratio of the acoustical stimulation signals to the electrical stimulation signals that are delivered to the recipient by adapting the operations of one or both of the electric sound processing path 146(A) or the acoustic sound processing path 146(B). In other words, by adapting the operations of one or both of the electric sound processing path 146(A) or the acoustic sound processing path 146(B) based on the sound signal attributes, the electro-acoustic adaption module 118 adjusts the output signals 159 and 169 relative to one another and, accordingly, adjusts the resulting electrical and acoustical stimulation relative to one another.

In accordance with the embodiments presented herein, the electro-acoustic adaption module 118 may be configured to adapt operations of one or both of the electric sound processing path 146(A) or the acoustic sound processing path 146(B) in a number of different manners. For example, in one arrangement, the electro-acoustic adaption module 118 is configured to dynamically adapt or modify the gain adjustments applied at one or both of the gain module 150 or the gain module 160 based on the sound signal attributes. Increasing the difference between the two gains will change the proportion of electrical stimulation versus acoustical stimulation levels being presented to the recipient.

Although FIG. 2 illustrates the adaption of gain adjustments at gain modules 150 and 160 preceding the filterbanks 152 and 162, respectively, it is to be appreciated that gain adjustments and real-time ratio adaption could alternatively be applied within, or after, the filterbanks 152 and 162. For example, the electro-acoustic adaption module 118 may also or alternatively adapt gain adjustments applied at the post-filterbank processing modules 154 and/or 164 (e.g., modifying channel gains applied at the post-filterbank processing modules). Modification of channel gains may result in boosts to the level or loudness of certain frequency components of the acoustical or electrical stimulation signals.

The modification of gain adjustments in the electric and/or acoustic sound processing paths 146(A) and 146(B) is one mechanism that may be employed by the electro-acoustic adaption module 118 to adapt the ratio of the acoustical and electrical stimulation signals. Further methods of adjusting the ratio between the acoustical and electrical stimulation may include, for example, adjusting the filterbank operations, adjusting the amount or type of noise reduction applied in each path (e.g., at post-filterbank processing modules 154 and/or 164), modifying other operations applied at the post-filterbank processing modules 154 and/or 164, modifying the channel selection rules utilized at channel selection module 156, modifying the channel mapping applied at mapping and encoding module 158, and/or modifying the re-synthesis operations at re-synthesis module 166.

As noted, the electro-acoustic adaption module 118 can set the ratio (e.g., the relative level and/or the loudness) of the acoustical stimulation signals to the electrical stimulation signals by adjusting the processing operations at different locations and in different manners in the electric and/or acoustic sound processing paths 146(A) and 146(B). As such, electro-acoustic adaption module 118 is shown connected to the various elements of each of the electric sound processing path 146(A) and the acoustic sound processing paths 146(B) by arrows 170. It is to be appreciated that the electro-acoustic adaption module 118 may perform adjustments that: (1) increase or decrease the level or loudness of only the acoustical stimulation signals, (2) increase or decrease the level or loudness of only the electrical stimulation signals, or (3) increase or decrease the level or loudness of both the acoustical stimulation signals and the electrical stimulation signals. In other words, setting at least one of a level or loudness of the acoustical stimulation signals relative to a level the electrical stimulation signals includes adjustments to the level or loudness of the acoustical stimulation signals, adjustments to the level or loudness of the electrical stimulation signals, or adjustments to the level or loudness of the acoustical stimulation signals and the electrical stimulation signals.

In certain examples, when setting the ratio of the acoustical stimulation signals to the electrical stimulation signals, the electro-acoustic adaption module 118 is configured to adjust a "balance" between the acoustical stimulation signals and the electrical stimulation signals. As used herein, adjusting the balance between the acoustical stimulation signals and the electrical stimulation signals refers to corresponding adjustments to both the acoustical stimulation signals and the electrical stimulation signals (i.e., increasing the loudness and/or level of one type of the stimulation signals, while corresponding decreasing the loudness and/or level of the other type of stimulation signals).

As noted, the electro-acoustic adaption module 118 operates by modifying operations of one or both of the electric sound processing path 146(A) or the acoustic sound processing path 146(B) for use in processing input sound signals, where the input sound signals are the triggering event for the modified operations. It is to be appreciated that the modified operations may be used to process the sound signals that triggered the change, and subsequent sound signals that share the same one or more triggering sound signal attributes. However, when the one or more triggering sound signal attributes are no longer detected or change, the processing may, for example, return to predetermined or preset operations, and/or make use of different operational adjustments.

FIG. 2 illustrates a specific arrangement that includes one signal analysis module 148. It is to be appreciated that alternative embodiments may make use of multiple signal analysis modules. For example, different sound signal analysis modules may be associated with different sound inputs, different processing paths, etc. In such embodiments, the electro-acoustic adaption module 118 is configured to utilize the information from each of the multiple signal analysis modules to set the ratio of the acoustic and electrical stimulation signals.

Figure 3:
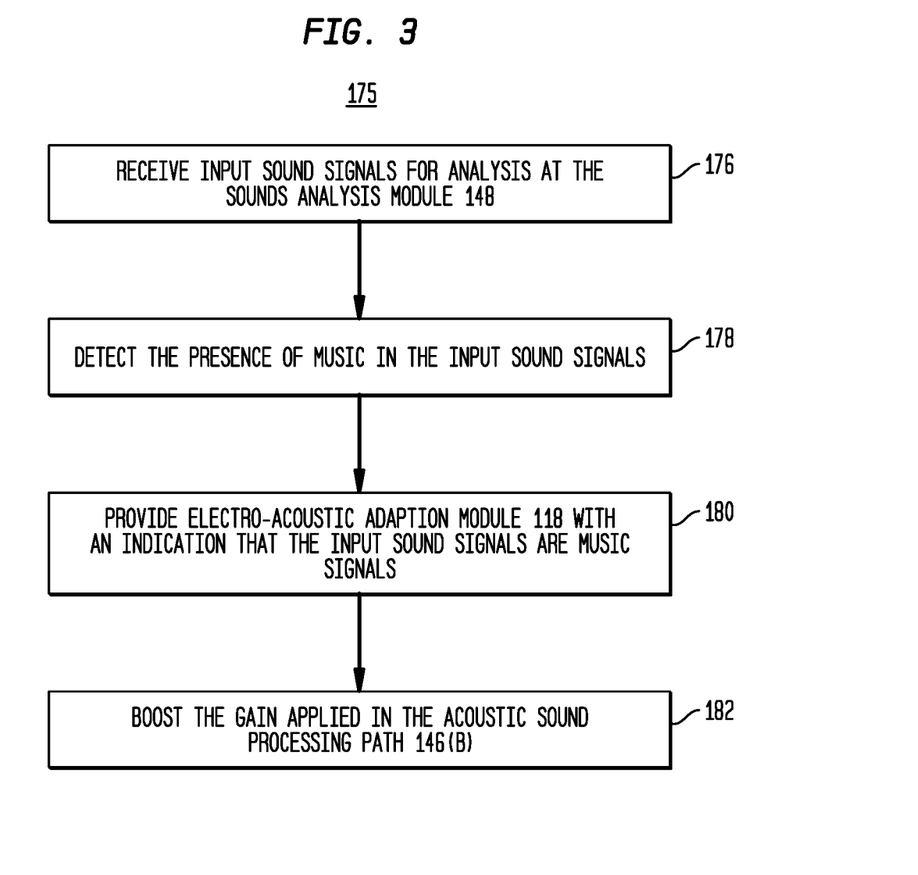
FIG. 3 is a flowchart of an example method executed by the sound processing unit of FIG. 2.

FIG. 3 is a flowchart illustrating one specific method 175 that may be performed by the sound processing unit 110 of FIGS. 1A, 1B, and 2. Method 175 begins at 176 where input sound signals received by the sound input elements 108 are provided to the sound analysis module 148. At 178, the sound analysis module 148 determines that the input sound signals are music signals (e.g., automatically detect signals with strong tonality and harmonics so as to classify the input signal type as "Music").

At 180, the sound analysis module 148 provides the electro-acoustic adaption module 118 with an indication that the input sound signals are music signals. Due to the presence of strong pitch and harmonic structures, music signals are better represented by the acoustic stimulation presented via the recipient's residual hearing. As a result, at 182, the electro-acoustic adaption module 118 increases or boosts the gain applied in the acoustic sound processing path 146(B) to enhance the recipient's perception of the tonality and harmonics present in the input sound signals. That is, since acoustical stimulation conveys a more natural sound and better indication of pitch, music appreciation may be improved by boosting the acoustical stimulation relative to the electrical stimulation.

In operation, the gain increases applied in the acoustic sound processing path 146(B) gain may continue as long as the sound analysis module 148 continues to classify the received sound signals as music signals. However, the gain increases are removed when the sound analysis module 148 ceases to classify the input sound signals as music signals (i.e., when the input signal type ceases to be music).

Although FIG. 3 illustrates the boosting of applied gain in the presence of music, it is to be appreciated that other parameters and/or operations within one or both of the acoustic sound processing path 146(B) and/or the electric sound processing path 146(A) may be alternatively or additionally adapted when music is identified in the sound signals. It is also to be appreciated that other acoustic scenes may result in a change in the ratio of acoustical stimulation signals to electrical stimulation signals in accordance with embodiments presented herein. For example, in scenes with moving noise sources, a higher proportion of the electrical stimulation signal (which typically contains more high frequency information) may aid the recipient in sound localization. Therefore, in such embodiments, adjustments may be made to one or both of the acoustic sound processing path 146(B) and/or the electric sound processing path 146(A) to increase one or more of the level or loudness of the electrical stimulation signals relative to the acoustical stimulation signals.

As noted, in other embodiments, one or both of the acoustic sound processing path 146(B) and/or the electric sound processing path 146(A) may be alternatively or additionally adapted based on an input level of the received sound signals, the detection of speech in the received signals, etc. For example, electrical stimulation signals are largely responsible for speech intelligibility, while the acoustic stimulation signals mostly provide presence. As such, in an embodiment in which speech is detected in the sound signals, the level or loudness of the electrical stimulation signals may be increased relative to the level or loudness acoustic stimulation.

Figure 4:
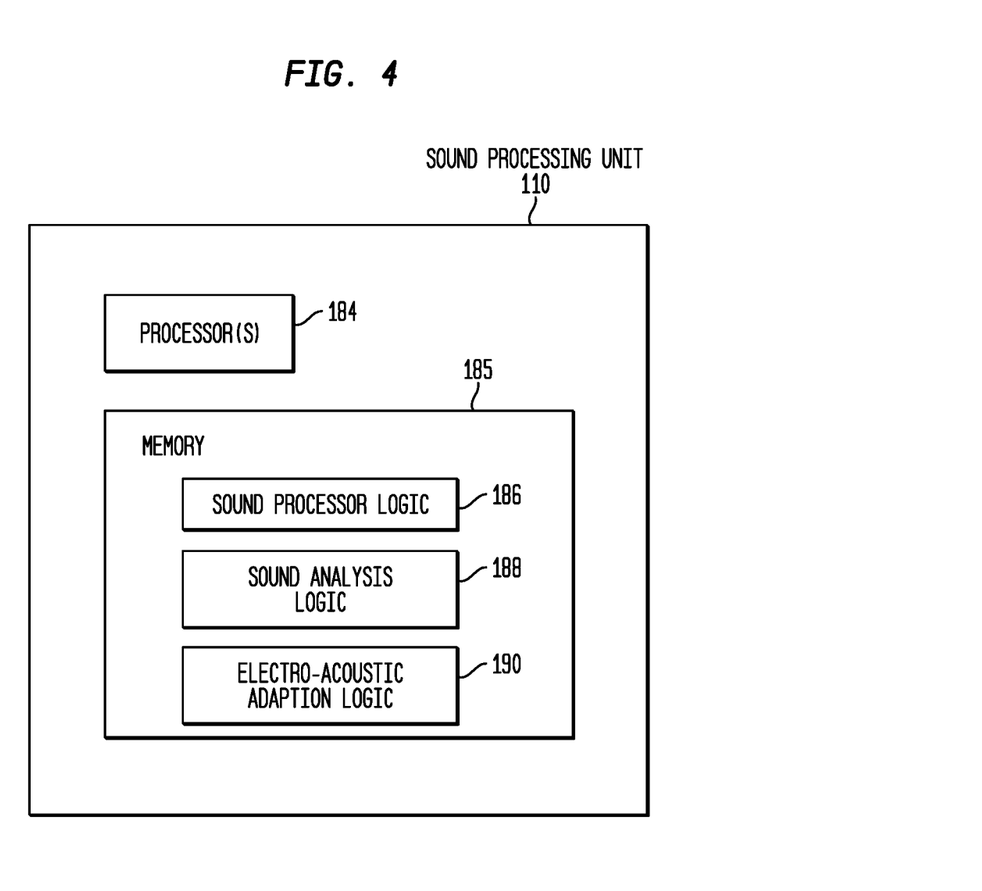
FIG. 4 is a block diagram of a sound processing unit in accordance with embodiments presented herein.

FIG. 4 is a schematic block diagram illustrating an arrangement for a sound processing unit, such as sound processing unit 110, in accordance with an embodiment of the present invention. As shown, the sound processing unit 110 includes one or more processors 184 and a memory 185. The memory 185 includes sound processor logic 186, sound analysis logic 188, and electro-acoustic adaption logic 190.

The memory 185 may be read only memory (ROM), random access memory (RAM), or another type of physical/tangible memory storage device. Thus, in general, the memory 185 may comprise one or more tangible (non-transitory) computer readable storage media (e.g., a memory device) encoded with software comprising computer executable instructions and when the software is executed (by the one or more processors 184) it is operable to perform the operations described herein with reference to sound processor 112, sound analysis module 148, and electro-acoustic adaption module 118.

FIG. 4 illustrates software implementations for the sound processor 112, the sound analysis module 148, and the electro-acoustic adaption module 118. However, it is to be appreciated that one or more operations associated with the sound processor 112, the sound analysis module 148, and the electro-acoustic adaption module 118 may be partially or fully implemented with digital logic gates in one or more application-specific integrated circuits (ASICs).

Merely for ease of illustration, the electro-acoustic adaption module 118 and the sound analysis module 148 have been shown and described as elements that are separate from the sound processor 112. It is to be appreciated that the functionality of the electro-acoustic adaption module 118 and the sound analysis module 148 may be incorporated into the sound processor 112.

Figure 5:
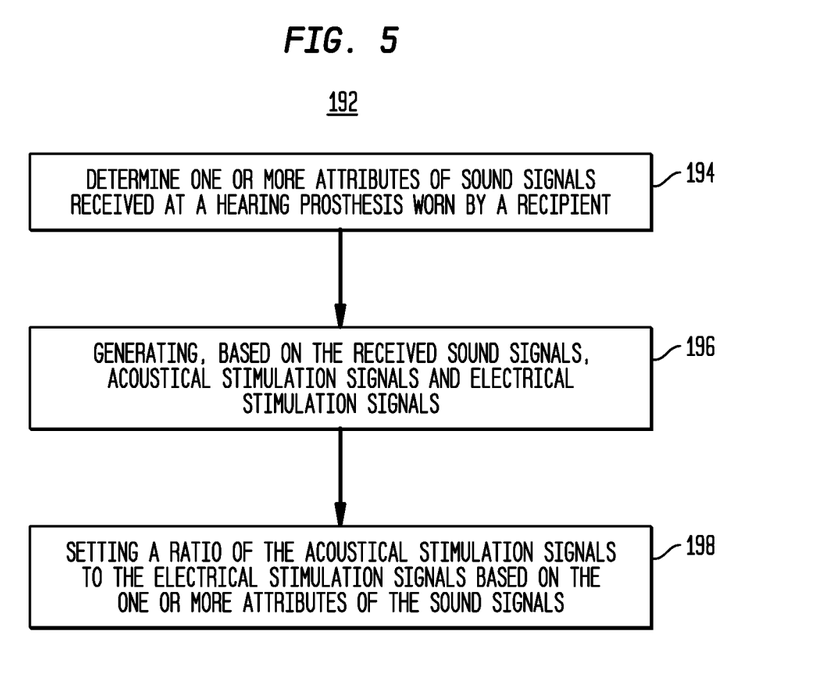
FIG. 5 is a flowchart of a method in accordance with embodiments presented herein.

FIG. 5 is a flowchart of a method 192 in accordance with embodiments presented herein. Method 192 begins at 194 where a hearing prosthesis determines one or more attributes of sound signals received at the hearing prosthesis. At 196, the hearing prosthesis generates, based on the received sound signals, acoustical stimulation signals and electrical stimulation signals. At 198, the hearing prosthesis sets a ratio of the acoustical stimulation signals to the electrical stimulation signals based on the one or more attributes of the sound signals.

As noted, embodiments of the present invention have been described herein with reference to one specific type of hearing prosthesis, namely an electro-acoustic hearing prosthesis comprising a cochlear implant portion and a hearing aid portion. However, it is to be appreciated that the techniques presented herein may be used with other types of hearing prostheses, such as bi-modal hearing prostheses, electro-acoustic hearing prosthesis comprising other types of output devices (e.g., auditory brainstem stimulators, direct acoustic stimulators, bone conduction devices, etc.).

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:
   determining one or more attributes of sound signals received at a hearing prosthesis worn by a recipient;
   generating, based on the received sound signals, acoustical stimulation signals and electrical stimulation signals; and
   dynamically setting, in real-time, a ratio of the acoustical stimulation signals to the electrical stimulation signals based on the one or more attributes of the sound signals.

2. The method of claim 1, wherein:
   determining the one or more attributes of the sound signals received at the hearing prosthesis system comprises determining a type of the sound signals; and
   wherein dynamically setting the ratio of the acoustical stimulation signals to the electrical stimulation signals comprises setting the ratio of the acoustical stimulation signals to the electrical stimulation signal based on the type of the sound signals.

3. The method of claim 2, wherein determining the type of the sound signals comprises:
   determining that the sound signals are music signals.

4. The method of claim 1, wherein:
   determining the one or more attributes of the sound signals received at the hearing prosthesis system comprises determining an input level of the sound signals; and
   wherein dynamically setting the ratio of the acoustical stimulation signals to the electrical stimulation signals comprises setting the ratio of the acoustical stimulation signals to the electrical stimulation signal based on the input level of the sound signals.

5. The method of claim 1, wherein:
   determining the one or more attributes of the sound signals received at the hearing prosthesis system comprises determining the presence of speech in the sound signals; and
   wherein dynamically setting the ratio of the acoustical stimulation signals to the electrical stimulation signals comprises setting the ratio of the acoustical stimulation signals to the electrical stimulation signal based on the presence of speech in the sound signals.

6. The method of claim 1, wherein dynamically setting, in real-time, the ratio of the acoustical stimulation signals to the electrical stimulation signals, comprises:
   increasing a gain applied to one or more frequency ranges of the sound signals used to generate the acoustical stimulation signals.

7. The method of claim 1, wherein dynamically setting, in real-time, the ratio of the acoustical stimulation signals to the electrical stimulation signals, comprises:
   setting a level of the acoustical stimulation signals relative to a level of the electrical stimulation signals based on the one or more attributes of the sound signals.

8. The method of claim 1, wherein dynamically setting, in real-time, the ratio of the acoustical stimulation signals to the electrical stimulation signals, comprises:
   setting a loudness of the acoustical stimulation signals relative to a level of the electrical stimulation signals based on the one or more attributes of the sound signals.

9. The method of claim 1, wherein dynamically setting, in real-time, the ratio of the acoustical stimulation signals to the electrical stimulation signals, the method comprises:
   adjusting a balance between the acoustical stimulation signals and the electrical stimulation signals based on the one or more attributes of the sound signals.

10. The method of claim 1, wherein the hearing prosthesis is an electro-acoustic hearing prosthesis.

11. A hearing prosthesis, comprising:
one or more sound input elements configured to receive sound signals;
an electric sound processing path configured to convert at least a first portion of the sound signals into one or more output signals for use in delivering electrical stimulation to a recipient;
an acoustic sound processing path configured to convert at least a second portion of the sound signals into one or more output signals for use in delivering acoustical stimulation to the recipient; and
an electro-acoustic adaption module configured to alter a relative perceptual loudness of at least one of the electrical stimulation and the acoustic stimulation based on one or more attributes of the sound signals.

12. The hearing prosthesis of claim 11, wherein to alter the relative perceptual loudness of at least one of the electrical stimulation and the acoustical stimulation, the electro-acoustic adaption module is configured to adjust operation of the electric sound processing path to at least one of increase or decrease the perceptual loudness of the electrical stimulation relative to the perceptual loudness of the acoustical stimulation.

13. The hearing prosthesis of claim 11, wherein to alter the relative perceptual loudness of at least one of the electrical stimulation and the acoustical stimulation, the electro-acoustic adaption module is configured to adjust operation of the acoustic sound processing path to at least one of increase or decrease the perceptual loudness of the acoustical stimulation relative to the electrical stimulation.

14. The hearing prosthesis of claim 11, wherein the one or more attributes of the sound signals include a type classification of the sound signals.

15. The hearing prosthesis of claim 11, wherein the one or more attributes of the sound signals include an input level of the sound signals.

16. The hearing prosthesis of claim 11, wherein the one or more attributes of the sound signals include the presence of speech in the sound signals.

17. The hearing prosthesis of claim 11, wherein the hearing prosthesis is an electro-acoustic hearing prosthesis.

18. The hearing prosthesis of claim 11, wherein the electric sound processing path is configured to apply a first gain to the first portion of the sound signals and the acoustic sound processing path is configured to apply a second gain to the second portion of the sound signals, and wherein to the electro-acoustic adaption module is configured to increase a difference between the first and second gains to alter the relative perceptual loudness of at least one of the electrical stimulation and the acoustic stimulation.

19. The hearing prosthesis of claim 11, wherein to alter the relative perceptual loudness of at least one of the electrical stimulation and the acoustic stimulation setting the ratio of the acoustical stimulation signals to the electrical stimulation signal, the electro-acoustic adaption module is configured to adjust a balance between the acoustical stimulation and the electrical stimulation.

20. A hearing prosthesis, comprising:
one or more sound input elements configured to receive sound signals; and
one or more processors configured to generate output signals representative of acoustical stimulation signals and electrical stimulation signals for delivery to a recipient of the hearing prosthesis,
wherein at least one of a relative level and a relative loudness of the acoustical stimulation signals to the electrical stimulation signals is dynamically set, in real-time, based on one or more characteristics of the sound signals.

21. The hearing prosthesis of claim 20, wherein the one or more features of the sound signals include a type classification of the sound signals.

22. The hearing prosthesis of claim 20, wherein the one or more features of the sound signals include an input level of the sound signals.

23. The hearing prosthesis of claim 20, wherein the one or more features of the sound signals include the presence of speech in the sound signals.

24. The hearing prosthesis of claim 20, wherein the one or more processors are configured to boost a gain applied to one or more frequency ranges of the sound signals used to generate the acoustical stimulation signals so as to increase the level of the acoustical stimulation signals relative to the electrical stimulation signals.

25. The hearing prosthesis of claim 20, wherein the one or more processors are configured to reduce a gain applied to one or more frequency ranges of the sound signals used to generate the acoustical stimulation signals so as to decrease the level of the acoustical stimulation signals relative to the electrical stimulation signals.

26. The hearing prosthesis of claim 20, wherein the hearing prosthesis is an electro-acoustic hearing prosthesis.

* * * * *